United States Patent [19]
Costa

[11] Patent Number: 4,915,973
[45] Date of Patent: Apr. 10, 1990

[54] METHOD FOR TREATING SKIN DISEASES

[76] Inventor: António Costa, Rua Bernardo Santareno, Bloco C, 19-r/chao B, Miratejo, Corroios, Seixa, Almada, Portugal

[21] Appl. No.: 184,049

[22] Filed: Apr. 20, 1988

[30] Foreign Application Priority Data

Apr. 24, 1987 [PT] Portugal .................................. 84755

[51] Int. Cl.⁴ .............................................. A61K 33/36
[52] U.S. Cl. .................................... 424/667; 514/863; 514/861
[58] Field of Search .................. 424/150, 154, 667; 514/568, 863

[56] References Cited

U.S. PATENT DOCUMENTS 1,609,710  10/1924  Gilmore ............................... 424/150

OTHER PUBLICATIONS

The Merck Index, 9th ed., pp. 31, 49, 661–662 (1976).
Handbook of Nonprescription Drugs, 5th ed. pp. 338–341 (1977).

*Primary Examiner*—Leonard Schenkman
*Attorney, Agent, or Firm*—Watson, Cole, Grindle & Watson

[57] ABSTRACT

A process for preparing a dermatological lotion comprises sequentially adding 160 to 240 g. salicylic acid, 160 to 240 g. alum powder and 45 to 55 tincture of iodine to 800 to 1200 ml. ethyl alcohol to provide a mixture, homogenizing the mixture, and then maintaining the homogenized mixture quiescent for at least one week.

2 Claims, No Drawings

METHOD FOR TREATING SKIN DISEASES

BACKGROUND OF THE INVENTION

The present invention relates to a pharmaceutical composition for treating skin diseases, namely, dermatitis, psoriasis and eczema, hair loss, etc., as well as to a process for its preparation and to a mode of use in treating such skin diseases.

Skin diseases, although generally benign, are nonetheless very annoying and their healing is frequently very difficult. Some of these diseases, such as psoriasis, seem to be incurable. Dermatology specialists claim they do not know of any drug which actually heals this disease.

The object of the present invention is to provide a pharmaceutical composition which effectively treats psoriasis and other skin diseases, such as eczema, dermatitis, etc.

SUMMARY OF THE INVENTION

The composition according to the invention consists of a homogeneous mixture of common alcohol, salicylic acid, alum and tincture of iodine, in the following proportions:
  alcohol: 800–1200 ml.
  salicylic acid: 160–240 g.
  alum (powder): 160–240 g.
  tincture of iodine: 45 to 55 ml.

The components are herein referred to according to their common names in the pharmaceutical practice. So, alcohol means pure ethanol (96%); alum means aluminum and potassium sulfate, widely used in pharmaceutical and medical practice as a caustic; tincture of iodine is the common iodine solution in ethanol used as a skin desinfectant. All these components are widely known by those skilled in the art, and so they are considered identified by their common names.

The process according to the invention for preparing the above-mentioned composition consists of mixing together and homogenizing the components at room temperature, in the following order:
  1st - alcohol
  2nd - salicylic acid
  3rd - alum, and
  4th - tincture of iodine A brown, viscous liquid is obtained. This liquid is kept quiescent for at least 7 days before being used. After that it is ready for use.

As previously stated, the composition according to the invention is suitable for healing several dermatological diseases. It has proved particularly suitable in treating dermatitis, eczema, hair loss, and specially psoriasis.

The preferred regimen is two applications a day (preferably in the morning and at night) on the injured parts of the body.

The composition according to the invention is intended only for topical use.

Formulation example:

Dermatological lotion for topical application:

Components:

pure alcohol: 1000 ml.
  salicylic acid: 200 g.
  alum (powder): 200 g.
  tincture of iodine: 50 ml.

In a vessel containing the alcohol the other components are dissolved and then well mixed (homogenized) at room temperature, in the noted order. A brown, viscous liquid is obtained. This liquid is filled in bottles of the required size, which are kept quiescent for a week.

I claim:

1. A process of treating psoriasis, eczema and dermatitis by applying to the diseased skin a dermatological lotion which comprises a mixture of 800–1200 ml. ethyl alcohol, 160–240 g. salicylic acid, 160–240 g. alum powder, and 45–55 ml. tincture of iodine.

2. A process according to claim 1, wherein said dermatological lotion is applied to the diseased skin twice each day.

* * * * *